United States Patent [19]

Gosteli et al.

[11] Patent Number: 5,442,076
[45] Date of Patent: Aug. 15, 1995

[54] PROCESS FOR THE PRODUCTION OF 2-SUBSTITUTED-5-CHLORIMIDAZOLE-4-CARBALDEHYDES

[75] Inventors: Jacques Gosteli, Basel; Gareth Griffiths, Visp; René Imwinkelried, Brig-Glis, all of Switzerland

[73] Assignee: Lonza Ltd., Gampel/Valais, Switzerland

[21] Appl. No.: 92,052

[22] Filed: Jul. 15, 1993

[30] Foreign Application Priority Data

Jul. 16, 1992 [CH] Switzerland ................... 2239/92

[51] Int. Cl.⁶ ........................................... C07D 233/68
[52] U.S. Cl. ................................ 548/333.5; 548/316.4
[58] Field of Search .................... 548/316.4, 333.5

[56] References Cited

U.S. PATENT DOCUMENTS

| 4,355,040 | 10/1982 | Furukawa et al. | 548/336 X |
| 5,120,854 | 6/1992 | Alvarado et al. | 548/301 |

FOREIGN PATENT DOCUMENTS

| 0028834 | 5/1981 | European Pat. Off. |
| 0430709 | 6/1991 | European Pat. Off. |
| 0450566 | 10/1991 | European Pat. Off. |
| 2804435 | 8/1978 | Germany |
| 525676 | 8/1976 | U.S.S.R. ............... 548/333.5 |

OTHER PUBLICATIONS

Chemical Abstracts, vol. 116, (1992), 116:255614j.
Giles et al., Tetrahedron Letters, vol. 31, No. 6, (1990) pp. 5227 to 5230.
Katritzky et al., J. Org. Chem., 52, (1987), pp. 2726–2730.
R. Jacquier et al., Bull. Soc., Chim., France, (1971), No. 3 pp. 1040–1051.

*Primary Examiner*—Jacqueline Haley
*Attorney, Agent, or Firm*—Fisher, Christen & Sabol

[57] ABSTRACT

Process for the production of 2-substituted 5-chlorimidazole-4 carbaldehydes of general formula:

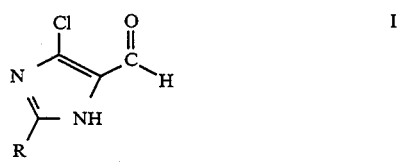

wherein R is alkyl, cycloalkyl, benzyl, or phenyl. These compounds form valuable intermediate products for the production of antihypertensive pharmaceutical agents or herbicidal compounds.

8 Claims, No Drawings

PROCESS FOR THE PRODUCTION OF 2-SUBSTITUTED-5-CHLORIMIDAZOLE-4-CARBALDEHYDES

BACKGROUND OF THE INVENTION

1. Field Of The Invention

The invention relates to a new process for the production of 2-substituted-5-chlorimidazole-4-carbaldehydes of the general formula:

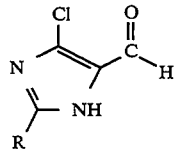

wherein R means an alkyl group, a cycloalkyl group, a benzyl group, or a phenyl group. The alkyl group can be straight-chained or branched $C_1$–$C_6$-alkyl groups, such as, methyl, ethyl, propyl, isopropyl, n-butyl, sec. butyl, tert. butyl, pentyl and hexyl groups. A preferred alkyl group is the n-butyl group. Cyclopropyl, cyclobutyl, cyclopentyl and cyclohexyl groups are representatives of the cycloalkyl group. Both the benzyl and the phenlyl group can contain substituents, such as, the aforementioned alkyl groups plus halogen atoms, nitro groups and amino groups.

2. Background Art

Several methods for the production of the mentioned compounds according to general formula I are known.

U.S. Pat. No. 4,355,040 describes a process according to which 2-amino-3,3-dichloro-acrylonitrile is reacted with an aldehyde to the corresponding azomethine intermediate product and further with an hydrogen halide and water to the 2-substituted-5-haloimidazole-4-carbaldehyde. Experimental data is lacking in such patent. But a great drawback of the synthesis is that the 2-amino-3,3-dichloroacrylonitrile used first has to be produced starting from dichloroacetonitrile by its reaction with hydrogen cyanide/sodium cyanide. The extremely toxic reactant and the safety measures associated with it that are already necessary for the preparation of the initial product, make the entire process unsuitable for industrial-scale production.

U.S. Pat. No. 4,355,040 discloses in another variant a three-stage process, in which, in a first stage, an amidinehydrochloride is ring closed with high $NH_3$ pressure with dihydroxyacetone, the imidazole alcohol is halogenated and finally oxidized to aldehyde. It turned out that pressures of over 20 bars are necessary for the ring closure reaction. The oxidation of the alcohol works according to U.S. Pat. No. 4,355,040 in the presence of chromium oxide.

It is obvious that an oxidation with heavy metal oxides, that are not recyclable as a rule, are no longer justifiable from present ecological aspects.

BROAD DESCRIPTION OF THE INVENTION

The main objective of the invention is to provide a process that does not have the above-mentioned drawbacks. Other objectives and advantages of the invention are set out herein or are obvious herefrom to one skilled in the art.

The objectives and advantages of the invention are achieved by the process and compound of the invention.

According to the process of the invention, a 2-substituted-3,5-dihydroimidazolin-4-one of the general formula:

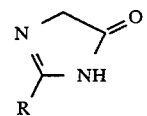

wherein R has the above-mentioned meaning, is reacted with phosphorous oxychloride and N,N-dimethylformamide to the desired 2-substituted 5-chlorimidazole-4-carbaldehyde.

The 2-substituted 5-chlorimidazole-4-carbaldehydes of the general formula I are important initial products for the production of antihypertensive pharmaceutical agents (U.S. Pat. No. 4,355,040) or of herbicidal compounds (German OS 2,804,435).

Preferably the 2-n-butyl derivative where R is n-butyl is used as the 2-substituted 3,5-dihydroimidazolin-4-one of general formula II. Preferably the reaction with phosphorous oxychloride and N,N-dimethylformamide takes place in a molar ratio of phosphorous oxychloride to N,N-dimethylformamide of 2 to 1 up to 4 to 1. Preferably the reaction takes place at a temperature between 50° and 80° C.

The invention also includes 2-n-butyl-3,5-dihydroimidazolin-4-one.

DETAILED DESCRIPTION OF THE INVENTION

The 2-substituted 3,5-dihydroimidazolin-4-ones of the general formula II are generally available in a known way, according to R. Jacquier et al., Bull. Soc. Chim. France, (1971), page 1040 f., by the reaction of a substituted imidic acid alkyl ester of the general formula:

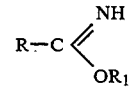

wherein R has the above-mentioned meaning and $R_1$ means a lower alkyl group having 1 to 4 C atoms with a glycine lower alkyl ester. Especially preferred within the context of the process according to the invention is the reaction of glycine ethyl ester with pentanimidic acid ethyl ester (general formula III with R being n-butyl and $R_1$ being ethyl) that synthesizes 2-n-butyl-3,5-dihydroimidazolin-4-one (general formula II with R being n-butyl). This compound is not known in the literature and therefore is also a component of the invention.

For the reaction to the desired 2-substituted 5-chlorimidazole-4-carbaldehyde of general formula I, it is suitable to proceed so that phosphorous oxychloride and N,N-dimethylformamide are first introduced in a molar ratio of 2 to 1 up to 4 to 1. The corresponding 2-substituted 3,5-dihydroimidazolin-4-one is then suitably added to the reaction mixture, whereupon the reaction advantageously takes place in a temperature range between 50° and 80° C.

The working-up of the end product can take place from ways known to one skilled in the art.

Preferably 2-n-butyl-5-chlorimidazole-4-carbaldehyde is produced according to the process according to the invention starting from 2-n-butyl-3,5-dihydroimidazolin-4-one.

EXAMPLE 1

2-n-butyl-3,5-dihydroimidazolin-4-one

A mixture of glycine ethyl ester (24.5 g, 221 mmol) and pentanimidic acid ethyl ester (34.5 g, 254 mmol) was left standing for 36 hours at −18° C. The precipitated product was filtered off, washed with ice cold diethyl ether (70 ml) and dried. The yield of the product was 10.51 g (34 percent). The product had a melting point of: 79.5° to 80.5° C. Other data concerning the product was:

$^1$H-NMR: (CDCl$_3$, 300 MHz) δ in ppm 9.3, 1H, br; 4.1, 2H, m; 2.48, 2H, t; 1.68, 2H, m; 1.45, 2H, m; 0.95, 3H, t

EXAMPLE 2

2-n-Butyl-5-chlorimidazole-4-carbaldehyde

N,N-dimethylformamide (3.65 g, 50 mmol) was instilled in POCl$_3$ (30.65 g, 200 mmol) at about 20° C. The reddish mixture was stirred for 15 minutes at 20° C. 2-n-Butyl-3,5-dihydroimidazolin-4-one (1.40 g, 10 mmol) was then added in portions and the mixture was heated for 1 hour at 80° C. Excess POCl$_3$ was removed on a rotary evaporator and the oily residue was poured on ice. The pH was adjusted to 7 with saturated NaHCO$_3$ solution and the mixture was extracted three times each with 150 ml of ethyl acetate. The combined organic phases were dried (MgSO$_4$), filtered and evaporated. Purification of the crude product by column chromatography on silica gel yielded 2-n-butyl-5-chlorimidazole-4-carbaldehyde. The yield of the product was 0.25 g, 14 percent, content about 95 percent ($^1$H-NMR).

What is claimed is:

1. Process for the production of a 2-substituted-5-chlorimidazole-4-carbaldehyde of formula:

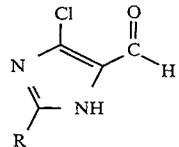

wherein R is an alkyl group, a cycloalkyl group, a benzyl group or a phenyl group, characterized in that a 2-substituted 3,5-dihydroimidazolin-4-one of formula:

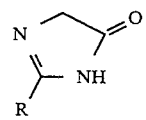

wherein R has the above-mentioned meaning, is reacted with phosphorous oxychloride and N,N-dimethylformamide to produce the end product.

2. The process according to claim 1 wherein R in the 2-substituted 3,5-dihydroimidazolin-4-one of formula II is n-butyl.

3. The process according to claim 2 wherein the reaction of the phosphorous oxychloride and the 2-substituted 3,5-dihydroimidazolin-4-one of formula II takes place in a molar ratio of the phosphorous oxychloride to the N,N-dimethylformamide of 2 to 1 up to 4 to 1.

4. The process according to claim 3 wherein the reaction takes place at a temperature between 50° and 80° C.

5. The process according to claim 1 wherein the reaction of the phosphorous oxychloride and the 2-substituted 3,5-dihydroimidazolin-4-one of formula II takes place in a molar ratio of the phosphorous oxychloride to the N,N-dimethyl-formamide of 2 to 1 up to 4 to 1.

6. The process according to claim 1 wherein the reaction takes place at a temperature between 50° and 80° C.

7. The process according to claim 4 wherein the 2-substituted 3,5-dihydroimidazolin-4-one is added to a mixture of the phosphorous oxychloride and the N,N-dimethylformamide.

8. The process according to claim 1 wherein the 2-substituted 3,5-dihydroimidazolin-4-one is added to a mixture of the phosphorous oxychloride and the N-N-dimethylformamide.

* * * * *